United States Patent
Klatt et al.

(10) Patent No.: US 6,300,521 B1
(45) Date of Patent: Oct. 9, 2001

(54) PROCESS FOR PREPARING OXOISOPHORONE

(75) Inventors: Martin Jochen Klatt, Bad Dürkheim; Thomas Müller, Dirmstein; Bernhard Bockstiegel, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/598,243

(22) Filed: Jun. 21, 2000

(30) Foreign Application Priority Data

Jun. 25, 1999 (DE) .............................. 199 29 367

(51) Int. Cl.$^7$ .................... C07C 45/00; C07F 13/00; B01J 31/00
(52) U.S. Cl. .................... 568/312; 568/320; 568/344; 568/360; 556/32; 556/45; 502/150
(58) Field of Search .................... 568/312, 320, 568/344, 360; 556/32, 45; 502/150

(56) References Cited

U.S. PATENT DOCUMENTS 4,026,947   5/1977   Costantini et al. ............. 260/586

FOREIGN PATENT DOCUMENTS

| 26 10 254 | 9/1976 | (DE) . |
| 2 303 785 | 10/1976 | (FR) . |
| 01 090150 | 4/1989 | (JP) . |
| 1090 150 | 4/1989 | (JP) . |

OTHER PUBLICATIONS

Constantini et al. "Selective Oxidation of 3,5,5–Trimethyl-cyclohexene–3 on (β–Isophorone) to 3,5,5–Trimethylecyclohexene–1,4, dione by oxygen catalyzed by Mn$^{II}$ or CO$^{II}$ chelates" Journal of Molecular Catalysts vol. 7, (1980) pp. 89–97.

Primary Examiner—Porfirio Nazario-Gonzalez
(74) Attorney, Agent, or Firm—Keil & Weinkauf

(57) ABSTRACT

The present invention relates to a process for preparing 3,5,5-trimethylcyclohex-2-ene-1,4-dione (oxoisophorone; OIP) by oxidation of 3,5,5-trimethylcyclohex-3-en-1-one (β-isophorone, β-IP) with molecular oxygen in the presence of a solvent, of a base and of a manganese salen derivative as catalyst.

7 Claims, No Drawings

PROCESS FOR PREPARING OXOISOPHORONE

The present invention relates to a process for preparing 3,5,5-trimethylcyclohex-2-ene-1,4-dione (oxoisophorone; OIP) by oxidation of 3,5,5-trimethylcyclohex-3-en-1-one (β-isophorone, β-IP) with molecular oxygen in the presence of a solvent, of a base and of a manganese salen derivative as catalyst.

Oxoisophorone (OIP) can be used as flavoring or fragrance in foodstuffs or in cosmetic formulations. OIP is moreover an intermediate for preparing vitamins and carotenoids.

It is known to prepare OIP by oxidation of β-isophorone (β-IP) with molecular oxygen in the presence of an inert solvent, of a base and of an Mn or Co salen derivative. DE Patent 2610254 C2 describes the use of a large number of cobalt(II) and manganese(II) salen derivatives as catalysts, it being possible to prepare the salen-like chelate ligands from a number of diamines and hydroxy carbonyl compounds. The list of hydroxy carbonyl compounds mentions, besides many others, also halogenated 2-hydroxybenzaldehydes with a widely variable substitution pattern. The conversions, yields and selectivities achieved in this process are often only low, especially on use of unsubstituted aromatic Mn and Co salens (ligands prepared from various diamines and 2-hydroxybenzaldehyde). Substitution with electron-attracting radicals on the aromatic system, such as introduction of a nitro group, leads, as shown in Example 5 loc. cit., to a lower yield.

JP 01090150 describes aromatic manganese(III) salen derivatives with a wide variability in the substitution pattern, the substituents, the counter ion and the number of C atoms in the amine bridge as catalysts in an analogous process. The best result is achieved on use of a chlorinated Mn(III) salen with X= acetate as counter ion with low precursor concentrations, giving yields of up to 90.7%. However, the low precursor concentrations mean that the space-time yield is likewise low.

In all prior art processes there is formation not only of high boilers, which interfere less with the purification, but also of the following identified byproducts IV (α-isophorone), V, VI and VII, which impede purification or further chemical reaction of the OIP:

IV

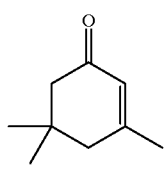

V

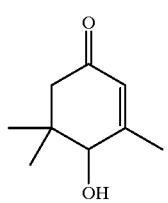

VI

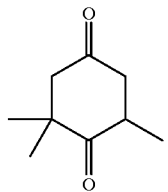

VII

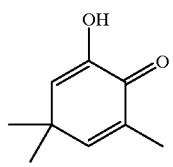

α-Isophorone (IV) is formed in a yield of up to 3.2% in the prior art processes, and compound V is formed in a yield of up to 4.4%. Compound VI particularly interferes with subsequent syntheses because it shows similar chemical behavior to the product OIP.

A disadvantage common to all the prior art processes is that as the precursor concentration increases the yields become low, and thus the space-time yields are only low, for OIP.

In addition, all the known processes use from the large number of possible combinations of bases and solvents triethylamine as base, frequently combined with ethers such as diglyme (dimethyldiglycol) as solvent. Since this mixture has an ignition point of 0° C., the known processes can be carried out on the industrial scale only with great safety precautions for this reason too.

It is an object of the present invention to remedy the deficiencies described and to develop a process for the oxidation of β-isophorone with manganese salen complexes with optimized properties, which gives goods yields, selectivities and space-time yields, also on the industrial scale, even with high precursor concentrations.

We have found that this object is achieved by a process in which 3,5,5-trimethylcyclohex-2-ene-1,4-dione is prepared by oxidation of 3,5,5-trimethylcyclohex-3-en-1-one with molecular oxygen in the presence of a solvent, of a base and of a catalyst, wherein the catalyst used is a manganese salen complex of the formula I

I

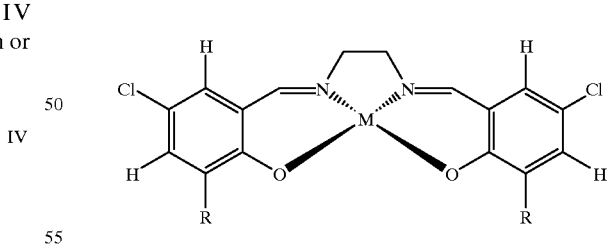

where
R is hydrogen or Cl and
M is Mn(II) or Mn(III)$^{(+)}$Cl$^{(-)}$.

The starting compound for the process is 3,5,5-trimethylcyclohex-3-en-1-one (β-isophorone; β-IP). The conversion to 3,5,5-trimethylcyclohex-2-ene-1,4-dione (oxoisophorone; OIP) takes place in a solvent by oxidation with molecular oxygen in the presence of a base and of the abovementioned catalyst of the formula I.

The catalysts of the formula I are manganese salen derivatives which are disubstituted or tetrasubstituted by chlorine and consist of the central manganese atom in oxidation state II or III and the appropriate tetradentate chelate ligand (salen ligand) disubstituted or tetrasubstituted with chlorine. The salen ligand can be prepared in a manner known per se from ethylenediamine and 5-chloro-2-hydroxybenzaldehyde or 3,5-dichloro-2-hydroxybenzaldehyde. Manganese in oxidation state III in the complex carries a chloride ion as negatively charged counter ion. The manganese(II) salen complexes of the formula I with R=H or Cl are prepared in a manner known per se, for example by reacting the appropriate salen ligands with $MnSO_4$. The manganese(III) salen complexes of the formula I with R=H or Cl and chloride as counter ion are prepared in a manner known per se, for example by reacting the appropriate salen ligands with $Mn(OAc)_3$ and LiCl.

Solvents mean organic solvents and water. Examples of organic solvents are optionally halogenated aliphatic or aromatic hydrocarbons, such as pentane, hexane, technical hexane, heptane, benzene, toluene, xylene, technical xylene, methylene chloride, chloroform, ethers such as dimethyl ether, diethyl ether, THF, dioxane, diglycol, dimethyldiglycol (diglyme), alcohols such as methanol, ethanol, propanol, ketones such as acetone, esters such as ethyl acetate, nitriles such as acetonitrile, or carboxamides such as dimethylformamide (DMF), dimethylacetamide (DMA), N-methylpyrrolidone (NMP).

Preference is given to organic solvents with metal-complexing properties, i.e. organic solvents which comprise groups or atoms with electron donor properties, such as NMP, DMF or DMA.

DMF, DMA or NMP are particularly preferred as organic solvents because their mixtures with the bases mentioned below, especially tripropylamine, have a higher ignition point.

Bases mean Bronsted bases such as LiOH, NaOH, KOH, Li, Na or K alcoholates or quaternary ammonium hydroxide or $C_2$–$Cl_4$-dialkylamines such as dimethylamine, diethylamine, methylethylamine, dipropylamine, diisopropylamine, ethylbutylamine, dibutylamine or $C_3$–$C_{20}$-trialkylamines such as trimethylamine, triethylamine, tripropylamine or tributylamine.

$C_3$–$C_{20}$-Trialkylamines are preferred bases.

The use of tripropylamine as base is particularly preferred because the mixture with DMF or DMA has a higher ignition point.

Combinations of tripropylamine as base and DMF or DMA as solvent therefore represent a preferred embodiment.

The concentration of the precursor β-IP in the process according to the invention is typically from 0.5 to 4.0 mol/l, in particular from 2.5 to 3.6 mol/l.

The reaction temperature is typically controlled at 20° C. in order to allow the highly exothermic reaction to proceed in a controlled manner.

The concentrations of the reagents and catalysts are not critical and are, typically, from 0.1 mol % to 5 mol %, in particular from 0.3 mol % to 0.7 mol %, for the catalyst and from 0.1 mol/l to 0.5 mol/l, in particular from 0.15 mol/l to 0.35 mol/l, for the base.

The reaction typically takes from 0.1 to 10 hours, in particular from 4 to 8 hours.

In order to make it possible to increase the β-IP concentration further and thus further increase the space-time yield, the process is carried out in a particularly preferred embodiment with an inverse reaction, i.e. with slow, continuous introduction of β-IP into the reaction mixture. The duration of the introduction is typically between one and eight hours, in particular 4 hours.

The process is distinguished by the following advantages compared with the prior art:

The process can be carried out economically also on an industrial scale, i.e. with high space-time yields.

Even with high concentrations of the precursor β-IP (3.5 mol/l) selectivities and thus also yields of up to 90% are achieved with 100% conversion. This means that the space-time yield is increased. The increase in selectivity is achieved by a reduction in the byproducts IV–VII which are normally difficult to remove.

The ignition point of the reaction mixture can be increased by a suitable choice of the base and of the solvent, which provides a further safety advantage.

The following examples illustrate the invention.

EXAMPLES 1–3
Preparation of the Catalysts

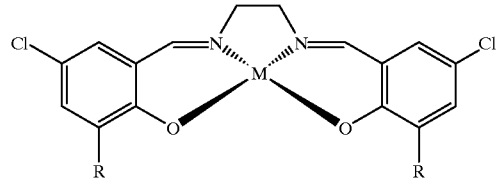

Iaa R = H, M = Mn(I)
Iab R = H, M = Mn(III) (+)Cl(-)
Ibb R = Cl, M = Mn(III) (+)Cl(-)

Example 1
Preparation of the Catalyst of the Formula Iaa 6.75 g (20 mmol) of the Schiff's base (salen ligand prepared from ethylenediamine and 5-chloro-2-hydroxybenzaldehyde) were dissolved in sodium hydroxide solution (1.6 g of NaOH in 100 ml of water) at 80 to 85° C. under nitrogen. A solution of 3.38 g (20 mmol) of $MnSO_4 \cdot H_2O$ in 15 ml of water was added dropwise to this solution over the course of 30 minutes, and the mixture was stirred at 85° C. until the Schiff's base had reacted completely (about 2 to 3 h; TLC check; cyclohexane/ethyl acetate 2:1). The reaction mixture was cooled to 10° C., and the orange-brown precipitate was filtered off and neutralized with water. The product was dried to constant weight in an oven at 50° C.

Yield: 7.4–7.7 g (94 to 99% of theory)

Example 2
Preparation of the Catalyst of the Formula Iab 6.75 g (20 mmol) of the appropriate Schiff's base (salen ligand prepared from ethylenediamine and 5-chloro-2-hydroxybenzaldehyde) were dissolved in 150 ml of boiling ethanol and, after addition of 5.36 g of $Mn(OAc)_3 \cdot 2H_2O$ (20 mmol), refluxed for three hours. Then three equivalents of lithium chloride (2.54 g, 60 mmol) were added and the reaction solution was boiled for another three hours. After cooling to room temperature, the brownish-black solid was filtered off and washed with MTB ether (100 ml). The complex is dried in vacuo at 50° C. overnight.

Yield: 8.40 g (99% of theory)

Example 3
Preparation of the Catalyst of the Formula Ibb

Preparation analogous to Example 3 with the difference that a salen ligand prepared from ethylenediamine and 3,5-dichloro-2-hydroxybenzaldehyde was used.

Yield: 95 to 99% of theory

Examples 4 to 8
Preparation of OIP by Oxidation of β-IP in the Presence of the Catalysts Iaa, Iab and Ibb and Various Solvents 520 ml of DMF or DMA (dimethylacetamide), 28.6 g of tripropylamine (0.2 mol) and about one third of the required amount of catalyst (total: 9 mmol in each case, 0.45 mol %) were introduced into a 1 L HWS glass reactor, and the temperature was maintained at 200° C. While passing in oxygen (with exit gas system) and controlling the temperature (20+/−1° C.), 276 g of β-isophorone (2.0 mol) were added dropwise over the course of 4 hours. The remaining amount of the catalyst was suspended in DMF or DMA, and portions were metered in after two, four and six hours. The gas was passed in for a total of eight hours.

The oxoisophorone yields were determined by gas chromatography using an internal standard (methyl benzoate). Besides the starting compound β-isophorone and the product oxoisophorone, the amount of the byproducts IV, V, VI and VII was determined by area integration of the gas chromatogram.

The reaction was carried out with various catalysts and solvents. The respective reaction conditions and results are compiled in Table 1.

Comparative Examples 1 and 2
Preparation of OIP in the Presence of Catalysts IIa, IIb and III

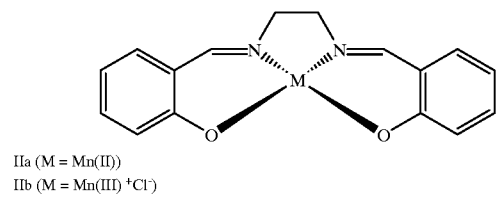

IIa (M = Mn(II))
IIb (M = Mn(III) $^{+}$Cl$^{-}$)

OIP was prepared in analogy to Examples 4 to 8 using catalysts IIa and IIb in DMF as solvent. The reaction conditions and results are summarized in Table 2.

TABLE 1

| Example | Catalyst | Solvent | Yield in [%] | | | | | |
|---|---|---|---|---|---|---|---|---|
| | | | OIP | β-IP | α-IP (IV) | V | VI | VII |
| 4 | Iaa | DMF | 86.2 | 0 | 1.6 | 1.9 | 0.3 | 1.7 |
| 5 | Iaa | DMA | 90.0 | 0 | 1.5 | 1.4 | 0.2 | 0.7 |
| 6 | Iab | DMF | 85.5 | 0 | 1.8 | 1.6 | 0 | 0.9 |
| 7 | Iab | DMA | 88.6 | 0 | 1.7 | 1.5 | 0 | 1.9 |
| 8 | Ibb | DMF | 89.3 | 0 | 1.8 | 1.9 | 0 | 1.2 |

TABLE 2

| Example | Catalyst | Solvent | Yield in [%] | | | | | |
|---|---|---|---|---|---|---|---|---|
| | | | OIP | β-IP | α-IP (IV) | V | VI | VII |
| 1 | IIa | DMF | 82.4 | 0.3 | 1.9 | 4.4 | 0.5 | 1.2 |
| 2 | IIb | DMF | 81.2 | 0 | 3.2 | 3.8 | 2.9 | 2.8 |

We claim:

1. A process for preparing 3,5,5-trimethylcyclohex-2-ene-1,4-dione by oxidation of 3,5,5-trimethylcyclohex-3-en-1-one with molecular oxygen in the presence of a solvent, of a base and of a catalyst, wherein the catalyst used is a manganese salen complex of the formula I

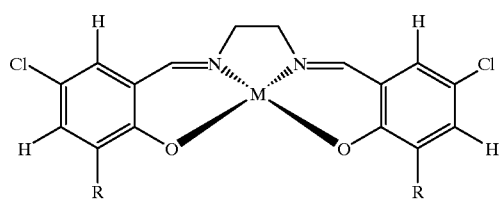

where

R is hydrogen or Cl and

M is Mn(II) or MN(III)$^{(+)}$Cl$^{(-)}$.

2. A process as claimed in claim 1, wherein a solvent with complexing properties is used as solvent.

3. A process as claimed in claim 1, wherein dimethylformamide (DMF), N-methylpyrrolidone (NMP) or dimethylacetamide (DMA) is used as solvent.

4. A process as claimed in claim 1, wherein a trialkylamine with 3 to 20 C atoms is used as base.

5. A process as claimed in claim 1, wherein tripropylamine is used as base.

6. A process as claimed in claim 1, wherein dimethylformamide (DMF) or dimethylacetamide (DMA) is used as solvent in combination with tripropylamine as base.

7. A process as claimed in claim 1, wherein an inverse reaction is carried out by feeding the precursor into the reaction mixture comprising the solvent, the base and the catalyst.

* * * * *